United States Patent [19]
Hommeltoft et al.

[11] Patent Number: 5,877,383
[45] Date of Patent: Mar. 2, 1999

[54] PROCESS FOR THE PREPARATION OF A HYDROCARBON PRODUCT BEING RICH IN MIDDLE DISTILLATE HYDROCARBON FRACTIONATION

[75] Inventors: Sven Ivar Hommeltoft, Hillerød; Annemarie Bauer, Copenhagen, both of Denmark

[73] Assignee: Haldor Topsoe A/S, Lyngby, Denmark

[21] Appl. No.: 964,770

[22] Filed: Nov. 5, 1997

[30] Foreign Application Priority Data

Nov. 5, 1996 [DK] Denmark ................................ 1237/96

[51] Int. Cl.$^6$ ........................................................ C07C 2/58
[52] U.S. Cl. .......................... 585/730; 585/458; 585/462; 585/721
[58] Field of Search ..................... 585/458, 462, 585/721, 730

[56] References Cited

U.S. PATENT DOCUMENTS

| | | | |
|---|---|---|---|
| 5,220,095 | 6/1993 | Hommeltoft et al. | 585/720 |
| 5,245,100 | 9/1993 | Hommeltoft et al. | 585/720 |
| 5,349,116 | 9/1994 | Kallenbach et al. | 585/730 |
| 5,498,820 | 3/1996 | Hommeltoft | 585/462 |

OTHER PUBLICATIONS

"Flexibility of a New Fixed–Bed Alkylation Technology Applying a Supported Liquid Superacid in a Moveable Catalyst Zone"; Symposium on New Chemistry with Solid–Acid Catalysts in the Alkylation of Isobutane with Olefins Presented Before the Division of Petroleum Chemistry, Inc., 212th National Meeting, American Chemical Society, Orlando Florida, Aug. 25–29, 1996, pp. 700–705; S.I. Hommeltoft.

*Primary Examiner*—Glenn Caldarola
*Assistant Examiner*—In Suk Bullock
*Attorney, Agent, or Firm*—Ostrolenk, Faber, Gerb & Soffen, LLP

[57] ABSTRACT

A process for the manufacture of a hydrocarbon mixture being rich in middle distillate products with the boiling part range of 175°–360° C. by alkylation of a hydrocarbon feed stock with an olefinic alkylating agent, comprises the steps of contacting a hydrocarbon feedstock and an olefinic alkylating agent with a catalyst composition containing an acid selected from the group of fluorinated alkane sulphonic acids having the general formula:

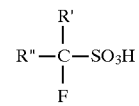

wherein
R'=F, Cl, Br, I, H, an alkyl or perfluoro alkyl group,
R"=H, alkyl, aryl or a perfluoro alkoxy group, and
recovering a product stream of alkylated hydrocarbons and optionally recycling to the reactor lower isoalkanes being formed during the alkylation.

1 Claim, 1 Drawing Sheet

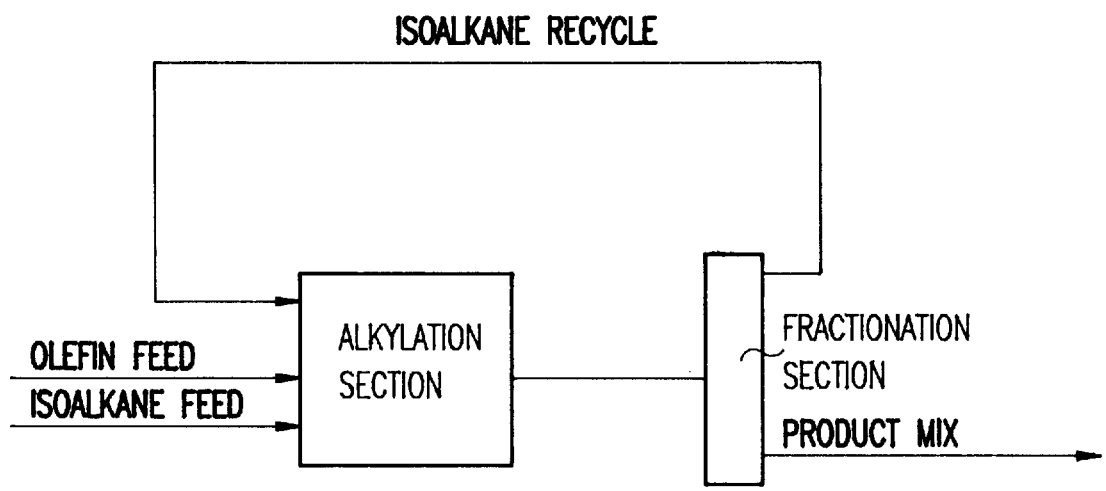

PROCESS FOR THE PREPARATION OF A HYDROCARBON PRODUCT BEING RICH IN MIDDLE DISTILLATE HYDROCARBON FRACTIONATION

FIELD OF INVENTION

The present invention is directed to preparation of hydrocarbon products boiling in the middle distillate range by alkylation of isoalkanes with lower olefins. Isobutane alkylation is conventionally used for the production of an alkylate product for use as gasoline blending. The alkylate product obtained thereby usually contains heavier products in an amount being too small for an economical recovery of middle distillate products. Middle distillate prepared by the invention is potentially useful as jet fuel, diesel additive or as solvent (S. I. Hommeltoft, ACS Petr. Chem. Div. Prep. 41 (1996) 700).

BACKGROUND OF THE INVENTION

U.S. Pat. No. 5,220,095 and U.S. Pat. No. 5,245,100 disclose a process for liquid phase alkylation of a hydrocarbon substrate with an olefinic alkylating agent in the presence of a fluorinated alkyl sulphonic acid catalyst supported on polar contact material.

U.S. Pat. No. 5,349,116 describes the use of triflic acid supported on a combination of aluminum borate and aluminum oxide as catalyst for the alkylation of alkane (preferably isobutane or isooctane) with olefins preferably 1-pentene or 1-hexene to obtain a product composition having a higher proportion in the middle distillate boiling range.

SUMMARY OF THE INVENTION

In accordance with the invention, a process for the manufacture of a hydrocarbon mixture being rich in middle distillate with the boiling part range of 175°–360° C. by alkylation of a hydrocarbon feed stock with an olefinic alkylating agent, comprises the steps of contacting a hydrocarbon feedstock and an olefinic alkylating agent with a catalyst composition containing an acid selected from the group of fluorinated alkane sulphonic acids having the general formula:

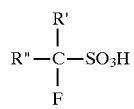

wherein

R'=F, Cl, Br, I, H, an alkyl or perfluoro alkyl group,

R''=H, alkyl, aryl or a perfluoro alkoxy group, and recovering a product stream of alkylated hydrocarbons and optionally recycling lower isoalkanes being formed during alkylation to the reactor.

In a specific embodiment of the invention, R' in the fluorinated alkane sulphonic acid is a fluorine atom, or a perfluoro alkyl group and R'' is a hydrogen atom.

The hydrocarbon feedstock can be contacted with the catalyst in a fixed bed of solid contact material. Thereby, the solid contact material is selected from a group of nonbasic refractory materials preferably silica. On the contact material, the catalyst is movably supported within a confined area thereof. The contact material may further comprise silica treated with boron phosphate or boron sulphate.

DETAILED DESCRIPTION OF THE INVENTION

In the typical process layout for a process for the alkylation of isobutane by lower olefins the reaction is performed in presence of a large excess of isobutane in order to ensure a good selectivity to high octane products in the gasoline boiling point range. Excess of isobutane is then separated from the product mixture by fractionation and recycled to the process. The general principle for an alkylation process according to the invention is illustrated in the drawings, wherein FIG. 1 shows a simplified process scheme of the alkylation process.

By the invention yield of products boiling in the middle distillate boiling point range is increased when recycling isobutane together with heavier isoalkanes (isopentane, isohexane, isoheptane, etc.), which usually are in the alkylate product withdrawn from fractionation section (FIG. 1). Thus, less amounts of products in the gasoline boiling point range and more amounts of heavier products boiling in the middle distillate boiling point range are recovered.

Replacement of one fluorine atom by a less electronegative group such as a hydrogen atom on the carbon atom in alpha-position to the sulphonic acid group increases the yield of middle distillate products. Thus, when employing the catalyst composition of this invention, the yield of middle distillate products in once through alkylation is increased considerably.

As an example use of a 1-hydro-1,2,2,2-tetrafluoroethane sulphonic acid in the above process, results in a high selectivity to middle distillate products even under conditions that with trifluoromethanesulphonic acid or pentafluoro-ethanesulphonic acid gives almost exclusively gasoline range products.

EXAMPLES

Comparison Example 1

A 100 ml reactor was packed with dried silica gel contact material of the type Merck 100, 0.2–0.5 mm particle size. 6 ml $CF_3SO_4$ were pumped into the reactor and adsorbed at the inlet on the materials. A feed stream containing 5% 2-butene in isobutane was then pumped through the reactor at a feed rate of 2.5 g/min. at temperatures varying in the range of 0°–30° C. The product composition was determined by gas chromatographic analysis (GC). The results are shown in Table 1.

TABLE 1

| Temperature, °C. | 0 | 10 | 20 | 30 |
|---|---|---|---|---|
| $C_{5-7}$, % (w/w) | 5 | 6 | 5 | 12 |
| $C_8$, % (w/w) | 89 | 85 | 82 | 75 |
| 125° C. < Bp < 150° C., % (w/w) | 1 | 1 | 1 | 2 |
| 150° C. < Bp < 175° C., % (w/w) | 1 | 2 | 2 | 2 |
| 175° C. < Bp < 300° C., % (w/w) | 3 | 4 | 5 | 5 |
| Bp > 300° C., % (w/w) | <0.1 | <0.1 | <0.1 | <0.1 |

Example 2

A 100 ml reactor was packed with dried silica gel of the type Merck 100, 0.2–0.5 mm particle size. 6 ml perfluorinated ethane sulphonic acid ($C_2F_5SO_3H$) were introduced into the reactor. A feed stream containing 5% 2-butene in isobutane was then passed through the silica gel contact material at a feed rate of 2.5 g/min. at temperatures varying in the range 0°–30° C. The product compositions was determined by GC analysis. The results are shown in Table 2.

TABLE 2

| Temperature, °C. | 0 | 10 | 20 | 30 |
| --- | --- | --- | --- | --- |
| $C_{5-7}$, % (w/w) | 6 | 5 | 10 | 14 |
| $C_8$, % (w/w) | 89 | 87 | 83 | 77 |
| 125° C. < Bp < 150° C., % (w/w) | 1 | 2 | 2 | 2 |
| 150° C. < Bp < 175° C., % (w/w) | 1 | 1 | 1 | 2 |
| 175° C. < Bp < 300° C., % (w/w) | 3 | 4 | 3 | 5 |
| Bp > 300° C., % (w/w) | <0.1 | <0.1 | <0.1 | <0.1 |

Example 3

A 100 ml reactor was packed with dried silica gel of the type Merck 100, 0.2–0.5 mm particle size. 6 ml $CF_3CFHSO_3H$ were pumped into the reactor and a feed stream containing 5% 2-butene in isobutane was pumped through the reactor at a feed rate of 2.5 g/min. at temperatures varying in the range 0°–30° C. The product compositions were determined by GC. The results are shown in Table 3.

TABLE 3

| Temperature, °C. | 0 | 10 | 20 | 30 |
| --- | --- | --- | --- | --- |
| $C_{5-7}$, % (w/w) | 10 | 11 | 13 | 15 |
| $C_8$, % (w/w) | 51 | 50 | 52 | 48 |
| 125° C. < Bp < 150° C., % (w/w) | 11 | 11 | 11 | 12 |
| 150° C. < Bp < 175° C., % (w/w) | 7 | 8 | 7 | 7 |
| 175° C. < Bp < 300° C., % (w/w) | 21 | 20 | 17 | 17 |
| Bp > 300° C., % (w/w) | <0.1 | <0.1 | <0.1 | <0.1 |

Example 4

A 100 ml reactor was packed with dried silica gel of the type Merck 100, 0.2–0.5 mm particle size. 6 ml $CF_3CFHSO_3H$ were pumped into the reactor and a feed stream containing 7% 2-butene and 3% isobutene in isobutane was pumped through the reactor at a feed rate of 2.5 g/min. at temperatures varying in the range 0°–30° C. The product compositions was determined by GC. The results are shown in Table 4. Table 4 shows also the result of a similar experiment with the same feed at 0° C. using 6 ml $CF_3SO_4H$ as catalyst.

TABLE 4

| Temperature, °C. | 0 | 10 | 20 | 30 |
| --- | --- | --- | --- | --- |
| Catalyst | $CF_3SO_4H$ | $CF_3CFHSO_3H$ | $CF_3CFHSO_3H$ | $CF_3CFHSO_3H$ |
| $C_{5-7}$, % (w/w) | 15 | 16 | 13 | 17 |
| $C_8$, % (w/w) | 64 | 33 | 33 | 35 |
| 125° C. < Bp < 150° C., % (w/w) | 6 | 13 | 12 | 13 |
| 150° C. < Bp < 175° C., % (w/w) | 4 | 7 | 7 | 6 |
| 175° C. < Bp < 300° C., % (w/w) | 11 | 31 | 34 | 29 |
| Bp > 300° C., % (w/w) | <0.1 | 0.4 | 0.5 | 0.4 |

We claim:

1. A process for the manufacture of a hydrocarbon mixture being rich in middle distillate products with the boiling point range of 175°–360° C. by alkylation of a hydrocarbon feed stock with an olefinic alkylating agent, comprising the steps of contacting a hydrocarbon feedstock and an olefinic alkylating agent with a catalyst composition containing an acid having the formula:

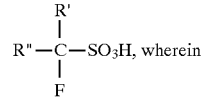

$R'=F$, $R''=H$, and recovering a product stream of alkylated hydrocarbons and optionally recycling to the reactor lower isoalkanes formed during the alkylation.

* * * * *